United States Patent [19]

Wilks

[11] 4,289,761

[45] Sep. 15, 1981

[54] COMBINATION OF 5-OXA-17-PHENYL-PGF$_1\alpha$'S ESTROGENIC COMPOUNDS FOR MENSES INDUCTION

[75] Inventor: John W. Wilks, Portage, Mich.

[73] Assignee: The Upjohn Company, Kalamazoo, Mich.

[21] Appl. No.: 175,466

[22] Filed: Aug. 6, 1980

[51] Int. Cl.$^3$ ............................................. A01N 45/00
[52] U.S. Cl. ............................................................. 424/240
[58] Field of Search ................................. 424/240, 238

[56] References Cited

U.S. PATENT DOCUMENTS 3,864,387  2/1975  Nelson ................................. 424/308
4,094,977  6/1978  Seeger et al. ....................... 424/240

Primary Examiner—Elbert L. Roberts
Attorney, Agent, or Firm—Lawrence T. Welch

[57] ABSTRACT

This invention provides a method for inducing menses and interrupting early pregnancy in female primate mammals, especially humans, which comprises the concomitant administration of a 5-oxa-17-phenyl-18,19,20-trinor-PGF$_1\alpha$, alkyl ester and an estrogenic compound. This invention further provides a pharmaceutical composition having these compounds as active ingredients. This method provides greater efficacy and safety as compared with the prior art.

8 Claims, No Drawings

COMBINATION OF 5-OXA-17-PHENYL-PGF$_1\alpha$'S ESTROGENIC COMPOUNDS FOR MENSES INDUCTION

DESCRIPTION

Background of the Invention

The present invention relates to a novel method of inducing menses and interrupting early pregnancy in female primates, particularly humans. This novel method involves the use of a combination of a prostaglandin and a compound having estrogenic activity. This invention also provides novel compositions to be used in this method.

The prostaglandins are derivatives of prostanoic acid, having the carbon atom numbering and structure as shown by formula I. A trivial system of nomenclature has been devised, which classifies the prostaglandins according to the substituents on the cyclopentane ring. See, N.A. Nelson, Journal of Medicinal Chemistry, 17:911 (1974). Thus, compounds of the PGF$\alpha$ series have the configuration shown in formula II. In the formulas herein, broken line attachments to the cyclopentane ring indicate substituents in the alpha configuration, i.e., below the plane of the ring. Solid line attachments indicate substituents in the beta configuration, i.e., above the plane of the ring. The prostaglandins involved in the present application are 5-oxa-17-phenyl-PGF$_1\alpha$, as well as alkyl esters and salts thereof.

The prostaglandins have a wide variety of pharmacological purposes. See, e.g., Bergstrom, et al., Pharmacol. Rev. 20:1 (1968) and references cited therein. One of the most important uses of the prostaglandins is in the area of reproductive medicine. Of particular relevance to the present invention is the use of prostaglandins for the induction of menses.

The present invention is concerned with the use of prostaglandins for menses induction. More particularly, the present invention relates to menses induction accompanied by pregnancy termination. Thus, the phrases "menses induction", "induction of menses", and the like are meant to include pregnancy termination if the subject is pregnant.

A disadvantage of the use of prostaglandins for the induction of menses in pregnant women is that the relatively large dosages necessary to induce menses with 100% efficacy have frequently caused side effects, such as fevers, nausea, and diarrhea.

Therefore, attempts have been made to combine prostaglandins with other compounds and with other prostaglandins in order to obtain a "synergistic" effect, thereby allowing for the use of smaller overall doses of the prostaglandin and other compound, reducing the side effects and increasing safety. Combinations of prostaglandins and other compounds have been successfully employed for certain purposes, mostly in lower animals. Thus, U.S. Pat. No. 4,094,977 discloses the use of a luteolytically active prostaglandin and at least one estrogen in a weight ratio of from 1:1 to 1:5,000 for use in synchronizing estrus in commercially reared animals. The prostaglandin-estrogen combinations disclosed in U.S. Pat. No. 4,094,977 are also disclosed as being useful for inducing labor in women.

One disadvantage of the process disclosed in the above-referenced patent is that estrogens, particularly the relatively large amounts of estrogens required therein, have certain risks attendant to their use. Problems associated with estrogen administration include the risk of endometrial cancer, tumors of the breast, cervix, vagina or liver, blood clots, excessive uterine bleeding, and fluid retention (affecting conditions such as asthma, epilepsy, migraine, and cardiac and renal disfunction). Because risks are generally associated with long term estrogen therapy, using high dosages, medical authorities and the estrogen manufacturers themselves recommend that the lowest dosages possible be employed.

In Saksena, et. al., Fertility and Sterility 26:126-130 (1975), it is disclosed that the combination of a 150 μg Intrauterine Silastic PVP implant of PGF$_2\alpha$ and a 4 μg injection of Depo®-Estradiol Cypionate (ECP) is 100% effective in inducing abortion in the rat.

Hixon, et al., in Biology of Reproduction 13:126 (1975) states that a combination of estradiol benzoate and PGF$_2\alpha$ is effective in decreasing progesterone in non-pregnant sheep.

Similarly, Shaikh, et al., reports that sequential treatment of non-pregnant cynomolgus monkeys with PGF$_2\alpha$ and estradiol-17$\beta$ is effective in inducing menses, see Prostaglandins 6:235 (1974). In another study, Shaikh reports that, sequential treatment of one monkey with estradiol-17$\beta$ and PGF$_2\alpha$ did result in an abortion, see Prostaglandins 2:227 (1972). In both cases, treatments overlapped by one day.

However, the teachings of prior art combinations for menses induction are of limited value in assessing the existence of primate luteolytic activity in that it is not possible to predict accurately the luteolytic activity of a compound or a combination in primates using rodent or other non-primate data. See, e.g., "The Use of PG's in Human Reproduction", Population Reports, Prostaglandins, Population Information Program, The Johns Hopkins University, Series G, No. 8 (March 1980) and J. W. Wilks, "A Procedure for Evaluating Luteolytic Agents in Primates," Ovarian Follicular and Corpus Luteum Function C. P. Channing, et al., Eds., Plenum Press pp. 757-766 (New York 1979). ("Luteolytic" agents are agents which cause corpus luteum regression. A functional corpus luteum is essential in early pregnancy).

Various control mechanisms exist governing corpus luteum function in mammalian species. The uterus regulates corpus luteum function in infraprimate animals, but the role of the uterus in primate luteal function has not been established. Thus, while PGF$_2\alpha$, a physiologic luteolytic substance of uterine origin, has been successfully employed to regulate estrous cycles of domestic animals (J. W. Lauderdale, et al., J. Anim. Sci. 38:964 (1974), it is ineffective in controlling the human corpus luteum (W. J. LeMaire, et al., Prostaglandins 1:259 (1972)).

An effective luteolytic method of inducing menses in female primates must be able to counteract the corpus luteum stimulating effects of chorionic gonadotropin. Agents which have been shown to be effective during nonfertile menstrual cycles have been ineffective during early gestation and in nonpregnant women given exogenous human chorionic gonadotropin (hCG). See, e.g., J. W. Wilks, supra, and references cited therein.

The difficulties posed in the prior art are solved by the method of the present invention which involves the use of a relatively non-toxic prostaglandin and a small amount of an estrogenic substance, such as mestranol, to induce menses in female primates, particularly women. The total dose of the prostaglandin-estrogenic substance combination is significantly lower than prior art methods. The "synergistic" effect of this combination increases safety while maintaining virtually 100% efficacy.

Prior Art

U.S. Pat. No. 4,094,977 discloses the use of at least one luteolytically active prostaglandin and at least one estrogen in a weight ratio of from 1:1 to 1:5,000 for use in estrous regulation in commercially reared animals and for labor-induction in women. U.S. Pat. No. 3,864,387 discloses the alkyl esters of 5-oxa-17-phenyl-18,19,20-trinor-PGF$_1\alpha$. Saksena, et al., Fertility and Sterility 26:126-130 (1975) discloses the use of PGF$_2\alpha$ and Depo ®-Estradiol Cypionate to induce abortion in the rat. Shaikh, et al., has disclosed the sequential use of PGF$_2\alpha$ and estradiol-17$\beta$ to induce menses in cynomolgus monkeys in Prostaglandins 2:227(1972) and Prostaglandins 6:253(1074). Hixon et al., has disclosed a luteolytic effect of a combination of PGF$_2\alpha$ and estradiol benzoate in non-pregnant sheep.

SUMMARY OF THE INVENTION

The present invention particularly provides a method for inducing menses in a female primate which comprises administering to said primate an amount effective to induce menses of (1) a prostaglandin of the formula III, wherein $R_{10}$ is hydrogen, alkyl of from one to 12 carbon atoms, or a pharmacologically acceptable cation, and (2) a compound having estrogenic activity, said combination being administered in a total dosage of from 0.1 and 50.1 mg per kg of body weight having between 0.1 and 50 mg per kg of body weight of the prostaglandin, and between 0.001 and 0.09 mg per kg of body weight of the estrogenic compound.

This invention also provides a pharmaceutical composition comprising as (1) a prostaglandin of the formula III wherein $R_{10}$ is hydrogen or alkyl of from one to 12 carbon atoms, or a pharmacologically acceptable cation; and (2) a compound having estrogenic activity, in a weight ratio of prostaglandin to estrogenic compound of from 10:9 to 50,000:1.

Esters within the scope of formula III include methyl, ethyl, propyl, butyl, pentyl, hexyl, octyl, nonyl, decyl, undecyl, dodecyl, and isomeric forms thereof.

The term "estrogenic compound" is meant to include any compound, natural or synthetic, which exhibits estrogenic activity in animals, particularly female primates. These compounds are generally steroids, but not all steroids have estrogenic activity, and thus all steroids cannot be employed in the method of this invention. Non-steroidal estrogenic substances may also be employed.

Examples of naturally occuring estrogens include: estriol-17$\beta$, estrone, estriol and their synthetic esters such as estradiol-17$\beta$-propionate, estradiol-17$\beta$-valeriate, estradiol, and 17$\beta$-($\beta$-cyclopentyl)-propionate.

Examples of synthetic compounds having estrogenic activity include: 17$\beta$-ethinyl-estradiol and the 3-ethers thereof, such as the 3-methyl- and 3-cyclopentyl ethers, and non-steroidal estrogenic substances, for example diethyl stilbestrol, hexestrol and dienestrol and the esters thereof, for example diethyl stilbestrol dipropionate, dipalmiate and diphosphoric acid ester, and the ethers thereof, for example diethyl stilbestrol methyl and dimethyl ethers. Numerous other compounds having estrogenic activity have also been disclosed. For a fuller discussion of estrogenic compounds, see Hogg, et al., "Synthetic Estrogens," Medicinal Chemistry, 2:34–217 (1956) and Loraine, et al., Hormone Assays and Their Clinical Application pp. 226–301 (1966).

An effective amount of the prostaglandin-estrogenic compound composition is the amount required for induction of menses in female primates with virtually 100% efficacy, without serious side-effects. Typically, the effective amount of this combination falls within the range of from about 0.001 to 0.09 mg per kg of the estrogenic compound and from about 0.1 to 50 mg per kg of body weight for the prostaglandin compound. Because of the possibility of side-effects with higher dosages, it is preferred to use a minimum amount of this combination. Thus, it is preferred to employ a total dose of from about 0.01 to about 0.05 mg per kg of body weight of the estrogenic compound and from about 0.1 to 5 mg per kg of body weight of the prostaglandin compound.

The "total dosage", as used herein, refers to the total amount of the prostaglandin-estrogen combination employed to achieve the desired result—i.e., menses induction. This dosage may be administered all at once, e.g., as a single injection, or over a short time period, e.g., injections every eight hours for several days.

To administer the preferred total dosage disclosed above a prostaglandin-estrogenic substance composition having a weight ratio of prostaglandin to estrogenic substance of from 2:1 to 500:1 can be used. It is most preferred to employ a composition having a weight ratio of prostaglandin to estrogenic substance of from 30:1 to 75:1.

The dose of the estrogen component of this invention will vary depending upon the biological potency of the natural or synthetic estrogen employed. Dose adjustments to achieve efficacious estrogenic activity may be based upon the biological activity of the particular estrogen as determined by established methods of estrogen bioassay. (See C. W. Emmens in R. I. Dorfman, Editor, "Methods in Hormon" Research, Vol. IIA, Bioassay," pp. 61–120, Academic Pres, New York, (1969)). Dosages described herein are based on estrogenic compounds having the approximate biologic potency of mestranol. When estrogenic compounds having estrogenic potency significantly higher or lower than mestranol are employed, the weight ratio of the estrogenic compound to the prostaglandin is correspondingly altered, in order that an equivalent amount of the estrogenic substance is administered.

A physician or veterinarian will readily determine the amount of this prostaglandin-estrogenic compound combination to be employed, based on the factors noted above.

These combinations may be administered using sterile pharmaceutical formulations suitable for intravenous infusion, subcutaneous injection, or intramuscular injection. The compounds of this invention may also be administered by nasal, oral, buccal, intravaginal, intracervical, intrauterine, and rectal means. These combinations may be formulated into slow release vehicles or polymers, such as silicone rubber, to form physical devices for subcutaneous, intravaginal, intracervical, or intrauterine administration.

While the method of this invention may be employed for inducing menses in all menstruating female primate, humans are the most preferred primates for the method of this invention.

Thus, the prostaglandin-estrogen combinations of the present invention are administered at any point in time during the reproductive time span starting at ovulation and continuing through the first trimester of pregnancy to advantageously terminate pregnancy and/or cause menstruation.

The method of this invention is advantageously employed in early pregnancy, when menses is delayed, or prior to the occurrence of menses.

The prostaglandin-estrogen combinations of the present invention are preferably administered up to the eighth week of pregnancy to inhibit corpus luteum function and effectively terminate pregnancy.

Thus the method and combinations of the present invention are effective in inducing menses during early pregnancy, just prior to expected menstruation, or when menstruation is delayed up to 90 days. The method and combinations of this invention are not efficacious in late pregnancy, particularly in the third trimester.

5-oxa-17-phenyl-18,19,20-trinor-PGF$_1\alpha$, methyl ester alone induces menses, but not at 100% efficacy at the lower dosages employed in the present invention. Further, these lower dosages allow for fewer of the undesirable side effects frequently associated with prostaglandins, e.g., nausea, fever, and diarrhea.

Estrogenic compounds alone do not interrupt pregnancy in primates when administered after the implantation of the fertilized ovum.

Thus, the virtual 100% efficacy of the combination of the present invention, at the relatively low dosages employed, represents a synergistic result when the activities of the individual compounds of the combination are considered.

While the compounds of the present invention may be administered simultaneously in the form of a combination, they may also be administered by separate single injections, as long as they are administered contemporaneously.

The 5-oxa prostaglandin analogs encompassed by formula III are used for the purposes described above in the free acid form, in ester form, or in pharmacologically acceptable salt form.

Pharmacologically acceptable salts of the formula III compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of the invention.

Pharmacologically acceptable amine cations are those derived from primary, secondary, or tertiary amines. Examples of suitable amines are methyl amine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

DESCRIPTION OF THE PREFERRED EMBODIMENTS

The operation of the present invention is seen more fully by the examples given below.

EXAMPLE 1

Induction of menses using 5-oxa-17-phenyl-18,19,20-trinor-PGF$_1\alpha$, methyl ester and mestranol 17 Female rhesus monkeys were placed with males from days 11 through 15 of the menstrual cycle. 5 ml blood samples were collected daily between 7:00 a.m. and 9:00 a.m. beginning on day 20 of the menstrual cycle and continuing until day 36 from the previous menses. Serum concentrations of monkey chorionic gonadotropin (mCG) were determined for each blood sample by radioimmunoassay. Pregnancy was confirmed in all monkeys prior to treatment by the qualitative determination of mCG in the serum. Treatments were initiated at 7:00 a.m. on day 28 from the previous menses and administered at 8 hr intervals thereafter. All treatments were given by intramuscular injection as an emulsion in one ml of vehicle. The vehicle employed was 4% glass distilled ethanol/96% sterile aqueous vehicle, containing 10 mg of carboxy-methylcellulose, 4 mg of polysorbate 80, and 0.42 mg of propylparaben per ml. 5-oxa-17-phenyl-18,19,20-trinor-PGF$_1\alpha$, methyl ester was administered at a dose of 7.5 mg per injection in all experiments. Mestranol was given at 100 micrograms or 200 micrograms per injection. When combination treatments were employed the prostaglandin and the mestranol were mixed in the same vehicle and given at the same injection site.

Part A

Three injections of prostaglandin and mestranol were given at 8 hr intervals to three monkeys. The dose of mestranol was 100 micrograms per injection. Pregnancy terminated in two monkeys and the serum hormone values for these animals showed a marked decline in progesterone to nearly undetectable levels within 24 hrs of the first injection. Pregnancy continued in one monkey.

Part B

The same procedure was followed as in the previous Example except that the dose of mestranol was increased to 200 micrograms per injection. The combination was given beginning at 7:00 a.m. of day 28 from the previous menses and administered at 8 hr intervals for a total of 9 injections. Pregnancy was summarily terminated in all three monkeys. Progesterone was nearly undetectable within 24 hrs of the first treatment, and estradiol and mCG had also declined markedly. After the treatment interval mCG was no longer detectable.

Part C

The same dosage as employed in Part B was used in this experiment, but only three injections of the combination were given. Pregnancy rapidly terminated following treatment for two monkeys, and serum progesterone and estradiol were nearly undetectable within 24 hrs of the first injection, and mCG declined on subsequent days to undetectable values. The third monkey also showed reduction in estradiol and progesterone, but progesterone rebounded. Serum mCG concentrations showed a normal pattern for early pregnancy. Despite these hormonal patterns the third monkey was no longer pregnant when examined two weeks after termination of daily blood sampling.

Part D

Following the regimen given above, three monkeys were given three 100 microgram injections of mestranol at 8 hr intervals. Three other monkeys were given 200 microgram injections of mestranol at 8 hr intervals. Serum paterns of mCG were normal in all monkeys. Serum estradiol fell to one third of pre-treatment values and progesterone declined by one half in both experiments. Serum concentrations of both steroids remained depressed throughout the remainder of the studies. Pregnancy did not terminate in any of the monkeys.

Part E 5-oxa-17-phenyl-18,19,20-trinor-PGF$_1\alpha$, methyl ester was administered using the regimen described above, for a total of 9 injections to each of two monkeys. Pregnancy terminated in one of the two monkeys.

Appetite depression was observed in most of the animals on the days of treatment with either the prostaglandin, estrogen, or the combination. The monkeys ate approximately half of the food provided. No other side-effects were seen.

The significant of the synergistic combination of the preceding example is highlighted by Example 2. As seen below, (15S)-15-methyl-PGF$_2\alpha$, methyl ester, a prostaglandin having high luteoyltic activity in infra primate species, does not synergistically combine with mestranol.

EXAMPLE 2

Induction of menses using (15S)-15-methyl PGF$_2\alpha$ methyl ester and mestranol

Part A

Following the procedure of Example 1, five pregnant rhesus monkeys were administered (15S)-15-methyl PGF$_2\alpha$ methyl ester and mestranol as follows. Two monkeys were given three injections containing 50 μg of the prostaglandin and 100 μg of mestranol and three monkeys were given three injections containing 50 μg of the prostaglandin and 200 μg of mestranol. Pregnancy terminated in two monkeys, one with the lower dose of mestranol and one with the higher dose of mestranol. Serum progesterone declined markedly in the two monkeys for which pregnancy terminated, and mCG was only five percent of normal. Serum progesterone was one half of normal for the remaining monkeys, and mCG was normal.

Anorexia and emesis was observed in one monkey.

Part B

Following the procedure of Part A, three injections containing 50 micrograms of (15S)-15-methyl-PGF$_2\alpha$ methyl ester alone were given to each of three pregnant rhesus monkeys. Pregnancy terminated in two of the three monkeys. Pregnancy terminated promptly in one of the monkeys, and the levels of serum progesterone and mCG were nearly undetectable 24 hours after treatment. In the other monkey for which pregnancy terminated, serum concentration of progesterone gradually decreased, and mCG failed to increase, and reached a value 10% that of normal in early pregnancy. In the third monkey (in which pregnancy continued), mCG decreased on the day after treatment, but subsequently returned to normal values. No side effects were observed.

FORMULAS

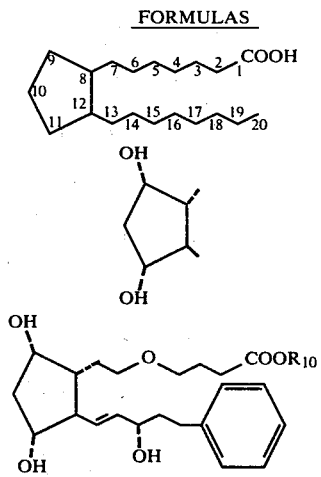

I claim:

1. A method for inducing menses in a female primate which comprises concomitantly administering to said primate an amount effective to induce menses of
  (1) a prostaglandin of the formula III

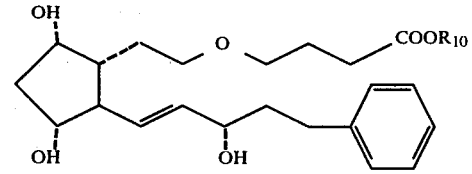

wherein R$_{10}$ is hydrogen, or alkyl of from one to 12 carbon atoms, or a pharmacologically acceptable cation; and (2) a compound having estrogenic activity;
said combination being administered in a total dosage of from 0.1 to 50.1 mg per kg of body weight, having between 0.1 and 50 mg of the prostaglandin and between 0.001 and 0.09 mg per kg of body weight of the estrogenic compound.

2. A pharmaceutical composition comprising
  (1) a prostaglandin of the formula III

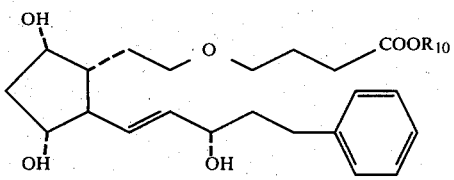

wherein $R_{10}$ is hydrogen, alkyl of from one to 12 carbon atoms or a pharmacologically acceptable cation; and (2) a compound having estrogenic activity, in a weight ratio of with respect to said prostaglandin of 10:9 to 50,000:1.

3. A method of claim 1, wherein said effective amount is 0.1 to 5 mg per kg of the prostaglandin and 0.01 to 0.05 mg per kg of the estrogenic compound.

4. A composition of claim 2, wherein the weight ratio of the prostaglandin compound to estrogenic compound is from 30:1 to 75:1.

5. A method of claim 3, wherein the prostaglandin compound is 5-oxa-17-phenyl-18,19,20-trinor-PGF$_1\alpha$, methyl ester and the estrogenic compound is mestranol.

6. A pharmaceutical composition of claim 4, wherein the prostaglandin compound is 5-oxa-17-phenyl-18,19,20-trinor-PGF$_1\alpha$, methyl ester and the estrogenic compound is mestranol.

7. A method of claim 3, wherein the prostaglandin compound is 5-oxa-17-phenyl-18,19,20-trinor-PGF$_1\alpha$, methyl ester and the estrogenic compound is ethinyl estradiol.

8. A pharmaceutical composition of claim 4, wherein the prostaglandin compound is 5-oxa-17-phenyl-18,19,20-trinor-PGF$_1\alpha$, methyl ester and the estrogenic compound is ethinyl estradiol.

* * * * *

UNITED STATES PATENT OFFICE
CERTIFICATE OF CORRECTION

Patent No. 4,289,761      Dated 15 September 1981

Inventor(s) John W. Wilks

It is certified that error appears in the above-identified patent and that said Letters Patent are hereby corrected as shown below:

Column 3, line 60, "17β-ethinyl-estradiol" should read -- 17α-ethinyl-estradiol --.

Column 7, line 44, "significant" should read -- significance --.

Signed and Sealed this

Second Day of November 1982

[SEAL]

Attest:

GERALD J. MOSSINGHOFF

Attesting Officer     Commissioner of Patents and Trademarks